(12) United States Patent
Sugimura

(10) Patent No.: US 9,533,131 B2
(45) Date of Patent: Jan. 3, 2017

(54) HOLLOW NEEDLELIKE OBJECT AND METHOD FOR MANUFACTURING HOLLOW NEEDLELIKE OBJECT

(71) Applicant: TOPPAN PRINTING CO., LTD., Tokyo (JP)

(72) Inventor: Hiroshi Sugimura, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 0 days.

(21) Appl. No.: 14/260,766

(22) Filed: Apr. 24, 2014

(65) Prior Publication Data

US 2014/0236075 A1 Aug. 21, 2014

Related U.S. Application Data

(63) Continuation of application No. PCT/JP2012/076696, filed on Oct. 16, 2012.

(30) Foreign Application Priority Data

Oct. 28, 2011 (JP) .................. 2011-236979

(51) Int. Cl.
*A61M 37/00* (2006.01)
*B29C 67/00* (2006.01)
*B29C 41/00* (2006.01)
*B29C 70/68* (2006.01)

(52) U.S. Cl.
CPC .......... *A61M 37/0015* (2013.01); *B29C 41/00* (2013.01); *B29C 67/00* (2013.01); *B29C 70/68* (2013.01); *A61M 2037/003* (2013.01); *A61M 2037/0038* (2013.01); *A61M 2037/0053* (2013.01); *A61M 2210/04* (2013.01)

(58) Field of Classification Search
CPC ............... A61M 2037/003; A61M 2037/0038; A61M 2037/0053; A61M 37/0015; B29C 41/00; B29C 70/68
See application file for complete search history.

(56) References Cited

U.S. PATENT DOCUMENTS 3,964,482 A    6/1976  Gerstel et al.
2010/0004608 A1*  1/2010  Hamamoto ....... A61M 37/0015
                                                604/272

FOREIGN PATENT DOCUMENTS

| EP | 2 359 885 A1 | 8/2011 |
| GB | 1 408 925 | 10/1975 |
| JP | 48-93192 | 12/1973 |
| JP | 2008-212458 | 9/2008 |
| JP | 2009-178531 | 8/2009 |
| JP | 2012-10735 | 1/2012 |

(Continued)

OTHER PUBLICATIONS

Chinese Office Action dated Jul. 3, 2015 in corresponding Chinese Patent Application No. 201280053053.9.

(Continued)

*Primary Examiner* — Kevin C Sirmons
*Assistant Examiner* — Deanna K Hall

(57) ABSTRACT

According to one embodiment, a method for manufacturing a hollow needlelike object including a hollow part inside includes: a step of preparing a first needlelike-object base having a face comprising a groove forming at least a part of the hollow part; and a step of covering the face of the needlelike-object base with a covering member.

17 Claims, 9 Drawing Sheets

(56) References Cited

FOREIGN PATENT DOCUMENTS

| KR | 10-2007-0060609 | 6/2007 |
|---|---|---|
| KR | 10-2009-0025937 | 3/2009 |
| WO | WO 2008/004597 A1 | 1/2008 |
| WO | WO 2008/013282 A1 | 1/2008 |
| WO | WO 2008/020632 A1 | 2/2008 |

OTHER PUBLICATIONS

International Search Report mailed Dec. 25, 2012 in corresponding International Patent Application No. PCT/JP2012/076696.
International Preliminary Report on Patentability mailed May 8, 2014, in corresponding International Patent Application No. PCT/JP2012/076696.
Extended European Search Report dated Nov. 17, 2015 in corresponding European Patent Application No. 12844586.3.

\* cited by examiner

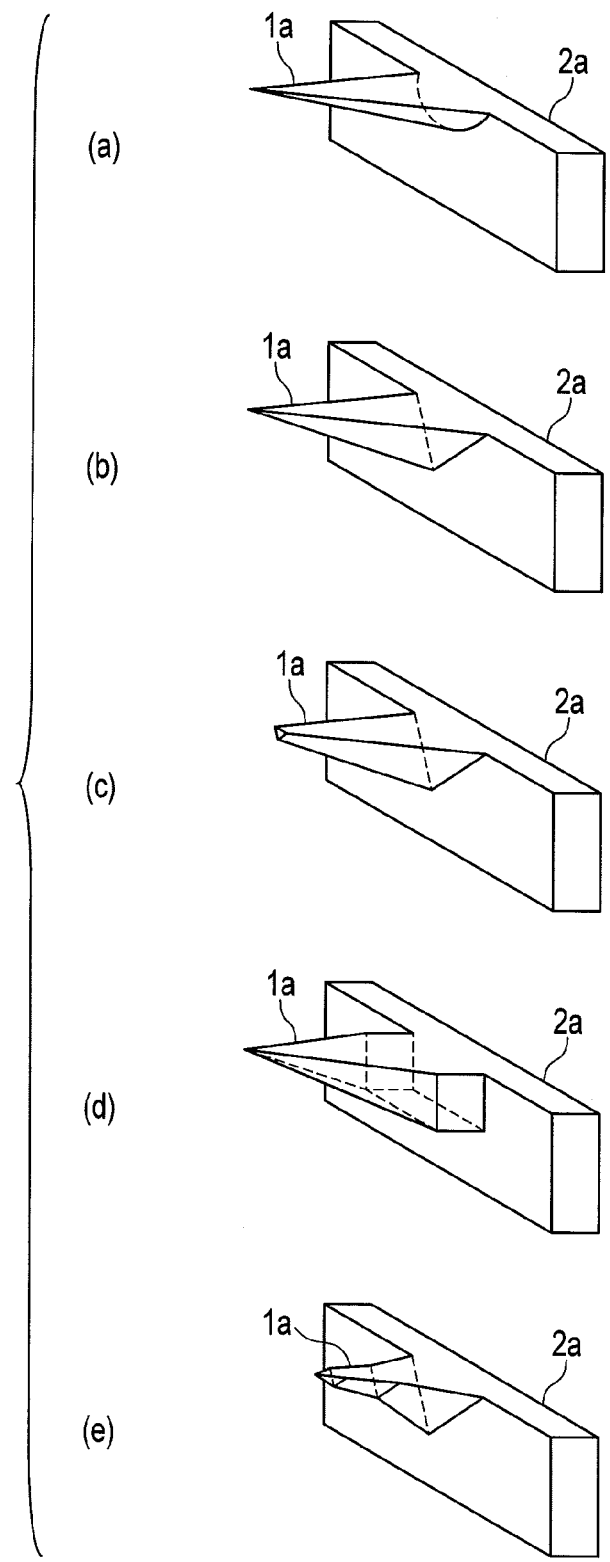
F I G. 1

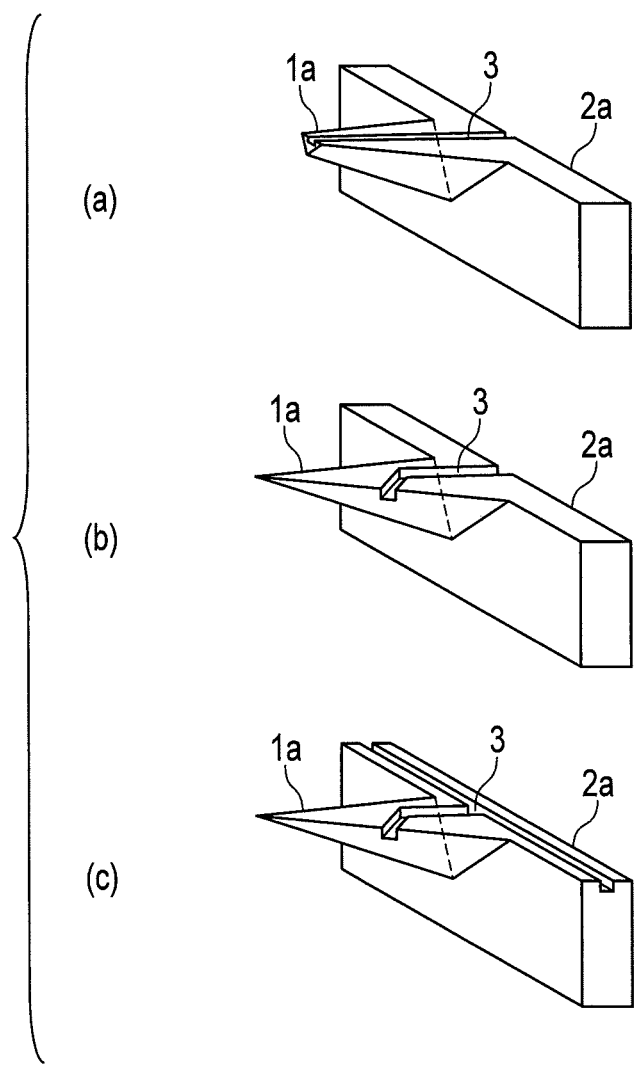
F I G. 2

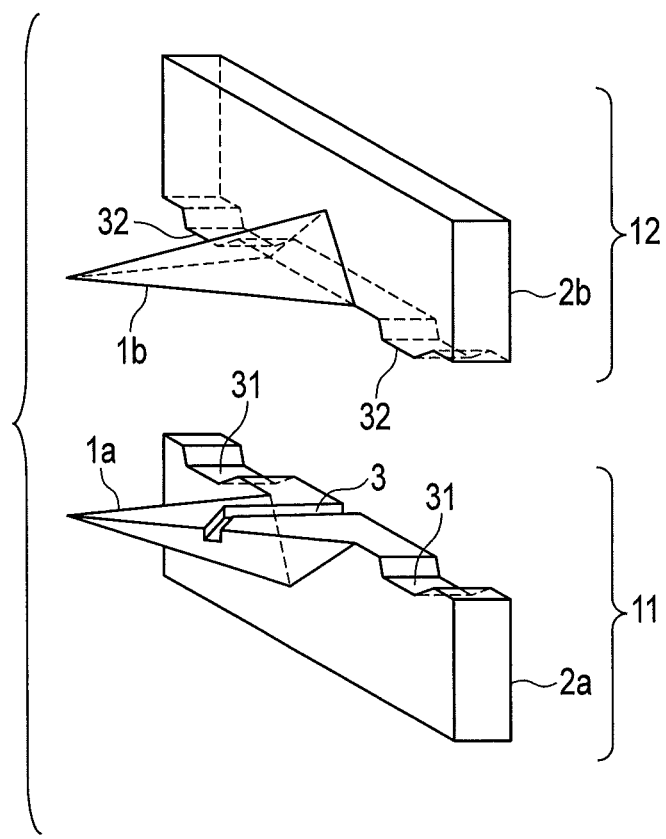
F I G. 5

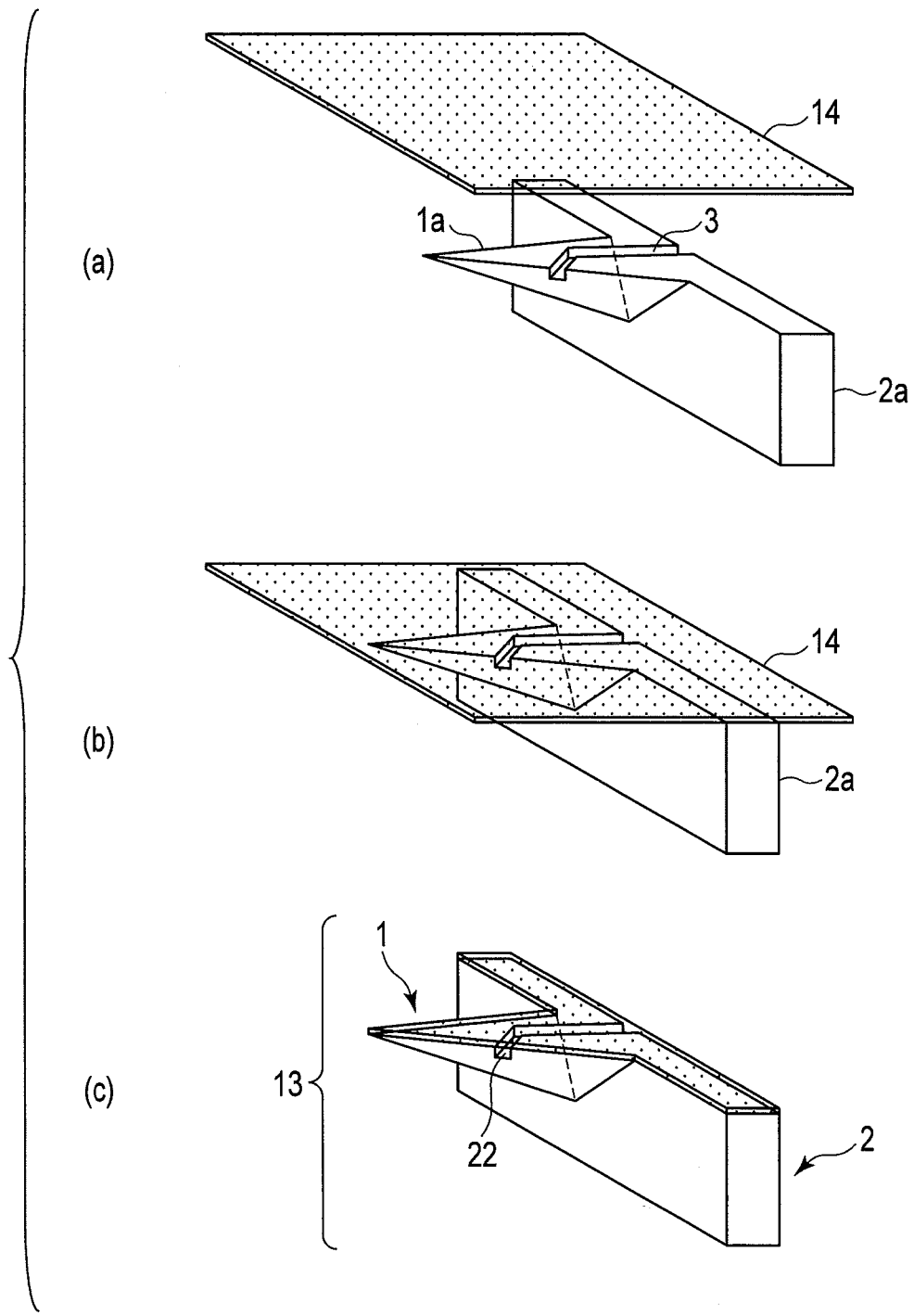
F I G. 6

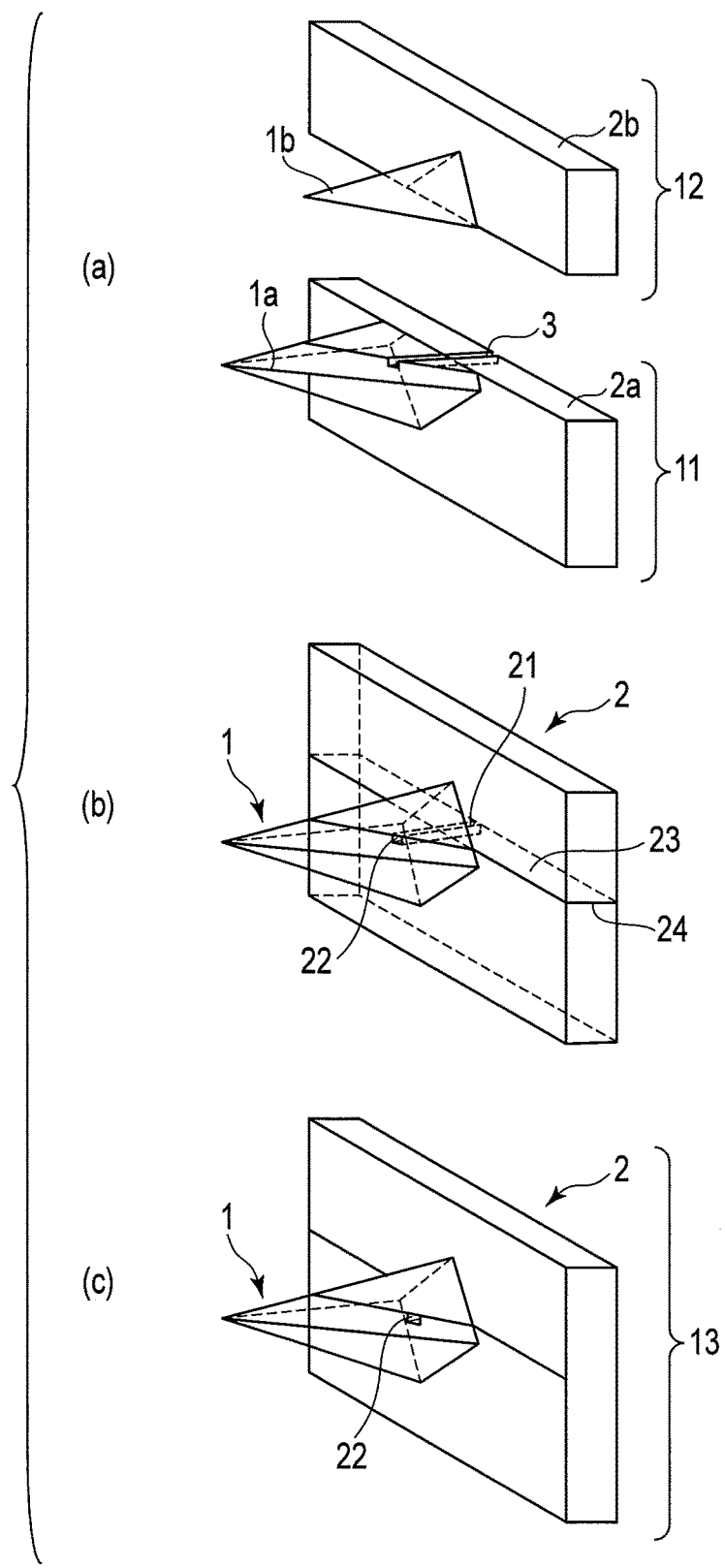
F I G. 9

HOLLOW NEEDLELIKE OBJECT AND METHOD FOR MANUFACTURING HOLLOW NEEDLELIKE OBJECT

CROSS-REFERENCE TO RELATED APPLICATION

This application is a Continuation Application of PCT Application No. PCT/JP2012/076696, filed Oct. 16, 2012 and based upon and claiming the benefit of priority from Japanese Patent Application No. 2011-236979, filed Oct. 28, 2011, the entire contents of all of which are incorporated herein by reference.

FIELD

The present invention relate to a hollow needlelike object and a method for manufacturing the hollow needlelike object.

BACKGROUND

Percutaneous absorption is method of delivering a material, such as a medicine, by permeating such through skin into a human body. In this method, the medication to be delivered to a human body can be delivered easily and without causing pain.

In the field of percutaneous medication, there has been proposed a method for delivering a medicine by puncturing skin with a needlelike object having a needle of the micrometer order (refer to Japanese Patent Application KOKAI Publication No. 48-93192).

There has also been proposed delivering a medication material through a hollow part by forming the hollow part in a needlelike object having a needle of the micrometer order (refer to the specification of U.S. Pat. No. 3,964,482).

There has also been proposed a method for manufacturing a needlelike object, which includes preparing an original plate through machining, forming a transfer plate from the original plate, and performing transfer process molding with use of the transfer plate (refer to the pamphlet of International Publication No. 2008/013282).

There has also been proposed another method for manufacturing a needlelike object, which includes manufacturing an original plate by an etching method, forming a transfer plate from the original plate, and performing transfer process molding with use of the transfer plate (refer to the pamphlet of International Publication No. 2008/004597).

The material forming a needlelike object is desirably a material which may not affect a human body even if the needlelike object should be broken and remain in a human body. Therefore, a biocompatible material, such as chitin or chitosan, has been proposed as the material of the needlelike object (refer to the pamphlet of International Publication No. 2008/020632).

BRIEF SUMMARY OF THE INVENTION

A conventional method for manufacturing requires a great number of process steps and much time and therefore has a problem of poor mass-productivity. Particularly, when a hollow needlelike object in which a plurality of needles are arrayed is manufactured, there is a difficulty in forming a hollow part of each needlelike object arranged with high precision.

When a hollow needlelike object is manufactured by use of a transfer molding method with excellent mass-productivity such as injection molding, a narrow long metal mold needs to be used for forming a hollow structure inside a micro needlelike object. However, there is also a difficulty in arranging a hollow structure inside a micro needlelike object by use of a narrow long metal mold. A metal mold for forming a narrow long hollow structure has poor strength, and causes a problem of short lifetime. Further, in a process of pulling off the narrow long metal mold for forming a hollow structure from a molded product after molding a hollow needlelike object, there is a problem that the metal mold is easily damaged.

The present invention has an object of providing a method for manufacturing a hollow needlelike object in a facilitated and mass-production manner, the hollow needlelike object including a groove surrounded with a covering member, by preparing a first needlelike-object base including a groove on its surface and the covering member, as divisional parts of the hollow needlelike object, and by covering the surface of the first needlelike-object base including the groove with the covering member, and of providing the hollow needlelike object manufactured by this method.

To solve the problem as described above, according to the first embodiment of the present invention, there is provided a method for manufacturing a hollow needlelike object comprising a hollow part inside, the method including; a step of preparing a first needlelike-object base having a surface comprising a groove forming at least a part of the hollow part; and a step of covering the surface of the needlelike-object base with a covering member.

In the method for manufacturing a hollow needlelike object, according to the first embodiment, the covering member is a second needlelike-object base or a sheet member and can form the hollow needlelike object in combination with the first needlelike-object base. When the covering member is combined with the first needlelike-object base, the covering member need not cover any part of the groove of the first needlelike-object base.

The second needlelike-object base may include a groove which forms the hollow part when combined with the groove of the first needlelike-object base.

At least one of the first needlelike-object base and the second needlelike-object base may include a needlelike object part and a base plate part which holds the needlelike object part on the bottom of the needlelike object part.

A groove connected to the groove of the needlelike object part may be formed in the base plate part.

In the method for manufacturing a hollow needlelike object, according to the first embodiment, the first needlelike-object base holds a plurality of needlelike object parts, arrayed in a row on a base plate part, and a plurality of hollow needlelike object parts arrayed in a row are obtained by using the first needlelike-object base.

Alternatively, a structure in which a plurality of more hollow needlelike objects are arrayed can be obtained by a step of preparing a plurality of hollow needlelike objects each manufactured by the method according to the first embodiment and a step of connecting base plate parts of the needlelike objects.

A step of processing a concave/convex structure in a connecting face of each of the base plate parts, for mutually aligning connecting positions, may be included prior to the step of connecting the base plate parts of the plurality of needlelike object parts to each other.

In the methods described above, a biodegradable material may be used for the material forming the first needlelike-object base and the covering member.

A surface treatment may be performed at least on a surface of the groove of the first needlelike-object base.

According to the second embodiment of the present invention, there is provided a hollow needlelike object manufactured by any of the methods for manufacturing a hollow needlelike object as described above.

According to the third embodiment of the present invention, there is provided a Liquid feed system for a hollow needlelike object including: the hollow needlelike object according to the second embodiment; and at least one of a liquid pump-out means and a liquid suction means connected to the hollow part of the hollow needlelike object.

According to the fourth embodiment of the present invention, there is provided a hollow needlelike object comprising a hollow part, wherein at least a first needlelike-object base and a covering member are joined together, and the first needlelike-object base includes a groove forming at least a part of the hollow part.

BRIEF DESCRIPTION OF THE DRAWINGS

FIG. 1 shows perspective views of a variety of examples of a first needlelike-object base material before forming a groove, for manufacturing a hollow needlelike object according to the embodiment of the present invention;

FIG. 2 shows perspective views of a variety of examples of the first needlelike-object base material having a groove, for manufacturing a hollow needlelike object according to the embodiment of the present invention;

FIG. 5 is a perspective view showing an engagement structure of a hollow needlelike object according to the third embodiment of the present invention;

FIG. 6 shows perspective views of a manufacturing process of a hollow needlelike object according to the fourth embodiment of the present invention;

FIG. 9 shows perspective views of a manufacturing process of a hollow needlelike object according to the seventh embodiment of the present invention.

DETAILED DESCRIPTION

Figure 3:
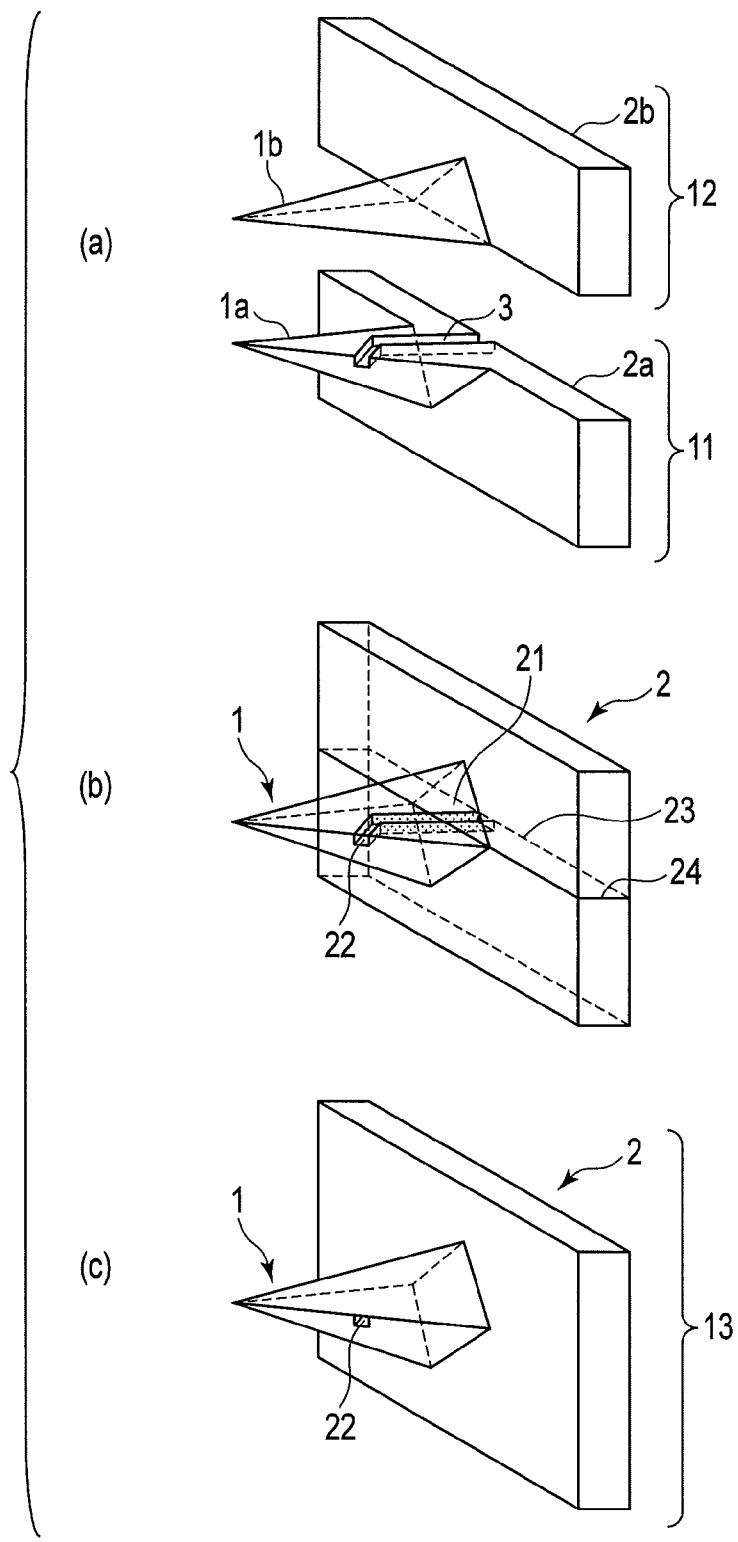
FIG. 3 shows perspective views of a manufacturing process of a hollow needlelike object according to the first embodiment of the present invention.

Hereinafter, a method for manufacturing a hollow needlelike object and a hollow needlelike object, according to embodiments of the present invention will be described.

According to an embodiment, a method for manufacturing a hollow needlelike object comprising a hollow part inside comprises: forming a first needlelike-object base on a surface thereof, the first needlelike-object base comprising a groove forming at least a part of the hollow part; and covering the surface comprising the groove of the first needlelike-object base with a covering member.

In a method for manufacturing a hollow needlelike object, according to an embodiment, a micro needlelike object comprising a hollow structure is not directly manufactured, but a groove finally forming at least a part of a hollow part in the first needlelike-object base is formed, and thereafter, a surface of the first needlelike-object base comprising the groove is covered with a covering member. Through such a process, a needlelike object comprising a hollow structure is manufactured. Thus, the first needlelike-object base comprising a surface where the groove is formed is manufactured firstly in the method for manufacturing a hollow needlelike object, according to the embodiment.

The first needlelike-object base comprising the groove can be manufactured by using a known micromachining technology. The micromachining technology can employ an appropriate combination of, for example, a lithography method, a wet etching method, a dry etching method, a sandblast method, a laser process, and a precision machining method.

The needlelike object may be manufactured by manufacturing a metal mold having a shape of a desired needlelike object structure subjected to concave-convex reversal through a micromachining technology or a shape obtained by concave-convex reversal of a metal mold through a transfer molding method. The material of the metal mold is not particularly limited insofar as the material has heat resistance, mechanical strength, and shape conformability. For example, silicon, glass, resins, or ceramics can be used for the material of the metal mold. A polymeric material is suitable for a transfer molding material. As a method for filling the metal mold with a polymeric material, a known transfer molding method can be used appropriately depending on a molding material used. For example, an injection molding method, an extrusion molding method, an imprinting method, or a casting method can be used as the transfer molding method.

The shape of the needlelike object can be designed and selected appropriately in accordance with purposes. The shape of the needlelike object may be, for example, a conical shape such as a circular cone or a pyramid, a truncated conical shape such as a truncated circular cone or a truncated pyramid, a columnar shape such as a round column or a prism, a shape obtained by obliquely truncating a distal end of a columnar shape, or a shape combining any of the foregoing shapes.

In manufacturing a hollow needlelike object according to any of the embodiments, the groove of the surface of the first needlelike-object base must be covered. For this reason, at least a surface of the shape of the first needlelike-object base where the groove is formed is flat. Specifically, the shape may be a shape obtained by cutting a structure along a plane including the center of the structure, the structure being a circular cone shown in FIG. 1(a), a triangular pyramid shown in FIG. 1(b), a truncated triangular pyramid shown in FIG. 1(c), a combination shown in FIG. 1(d) of a rectangular parallelepiped and a triangular pyramid, or a combination shown in FIG. 1(e) of triangular pyramids having different sizes.

In FIG. 1, the first needlelike-object base has a form in which a needlelike object part 1a is connected to and held on a flat base plate part 2a, at a bottom part thereof. However, manufacture of the hollow needlelike object according to the embodiments is not limited to this form. For example, the base plate part may be unused, the needlelike object part need not be held on the base plate part, or the base plate part need not always have a flat shape.

The length of the needlelike object can be appropriately selected in accordance with use purposes of the needlelike object. For the purpose of injecting a physiologically active substance into skin and picking up a living body sample from inside of the skin, the length of the needlelike object is desirably 20-2000 micrometers.

The groove formed in the first needlelike-object base may be appropriately designed without deviating from the shape and size of the needlelike object. The method for forming the groove is not particularly limited and any method capable of forming a desired groove can be appropriately selected. As a method for forming the groove, for example, a method can be used which appropriately combines a lithography method, a wet etching method, a dry etching method, a sandblast method, a laser process method, and a precision machining method.

Formation of the groove in the first needlelike-object base may be achieved by manufacturing a metal mold having a shape in a desired groove structure is subjected to concave-convex reversal by a micromachining technology. The groove may be formed by using the metal mold. The material of the metal mold is not particularly limited insofar as the material has heat resistance, mechanical strength, and shape conformability sufficient for use. The material of the metal mold may be, for example, metal, silicon, glass, resins, or ceramics. A polymeric material is suitable for the material of the needlelike object formed by a transfer molding method. A known transfer molding method may be appropriately selected as a method for filling the polymeric material in the metal mold, in accordance with the material used. The transfer molding method may be, for example, an injection molding method, an extrusion molding method, an imprinting method, or a casting method.

In particular, the first needlelike-object base and the groove can be molded simultaneously by selecting a molding method in which a metal mold for the first needlelike-object base and a metal mold for the groove are prepared firstly and then the two metal molds are positioned in relation to each other. Thus, the productivity of the needlelike object can be improved. In the case of molding by using this method, the injection molding method is particularly suitable.

In the method of using such two metal molds, various forms of grooves can be applied to the first needlelike-object base by appropriately designing patterns of the metal mold for the groove. For example, a flow channel can be formed linearly from the back face of the base plate to a distal end of the first needlelike-object base by forming a groove to be linear from the distal end of the needlelike-object base to the back face of the base plate. When the metal mold of the groove is not formed to reach the back face of the base plate, a non-through groove can be formed which penetrates the distal end of the first needlelike-object base.

In the method for manufacturing a hollow needlelike object, according to the embodiments, a part to form a hollow structure in the needlelike object can be formed by a planar groove process. Therefore, when the hollow part of the needlelike object is formed by a three-dimensional process, the methods according to the embodiments enable a complex flow channel to be easily formed, which would otherwise be difficult to achieve in practice. For example, application of a tapered shape to a flow channel, bending of a flow channel, L-form connection, and T type connection can be achieved easily.

Specifically, a groove 3 from the back face of a base plate part 2a to a distal end (truncated) of a needlelike object part 1a shown in FIG. 2(a) can be easily formed. Further, another groove 3 can be formed easily in which a flow channel has a linear groove shape from the back face of the base plate part 2a to an intermediate part of the needlelike object part 1a and is bent therefrom in a lateral direction to an outlet of the flow channel provided in an intermediate part of a joined needlelike object part 1, as shown in FIG. 2(b). Still another groove 3 can be formed easily in which the groove provided in the needlelike object part 1a, as shown in FIG. 2(c), is arranged to further extend in a lateral direction of the base plate part 2a, as shown in FIG. 2(c). By configuring a groove structure as shown in FIG. 2(c), two types of liquids can be fed from the flow channel outlet (an opening described later).

The polymeric material for molding the first needlelike-object base according to the transfer molding method is not particularly limited and a known polymeric material can be appropriately used. The polymeric material may desirably be, for example, polyethylene, polypropylene, polystyrene, or polycarbonate. Particularly, when the needlelike object is applied to a living body, a biodegradable polymer is desirably used. The biodegradable polymer is desirably, for example, poly ε-caprolactone, polyglycolic acid, or a copolymer of monomer of these polymeric materials and other monomer such as lactic acid.

First Embodiment

In a method for manufacturing a hollow needlelike object according to the first embodiment, a face comprising a groove of a first needlelike-object base as described above is covered with a second needlelike-object base as a covering member, and a needlelike object with a hollow structure formed inside can be thereby manufactured.

There is no particular limitation to the material or shape of the second needlelike-object base. When a needlelike object is applied to a living body, a biodegradable polymer is used desirably.

Next, a process of manufacturing a hollow needlelike object by covering the face of the first needlelike-object base comprising the groove with the second needlelike-object base will be described with reference to FIGS. 3(a), 3(b), and 3(c).

Firstly, as shown in FIG. 3(a), a first needlelike-object base 11 is prepared, which comprises a needlelike object part 1a and a base plate part 2a and comprises a groove 3 formed from the needlelike object part 1a to the base plate part 2a. The shape of the needlelike object part 1a can be designed appropriately. Here, the needlelike object part 1a has a shape obtained by dividing a right quadrangular pyramid having a truncated distal end by a face including a diagonal of a bottom face thereof and a center axis thereof (or the virtual apex of the pyramid).

In preparing the first needlelike-object base 11, a known high-precision process technology or micro machining technology can be used appropriately. For example, the high-precision process technology is used to prepare a needlelike object metal mold obtained by subjecting the shape of the needlelike object part 1a and base plate part 2a to concave-convex reversal and a groove metal mold obtained by subjecting the shape of the groove 3 to concave-convex reversal. Subsequently, the needlelike object metal mold and the groove metal mold are positioned facing each other, and then a polymer is injected and filled to obtain the first needlelike-object base 11 made of polymer with the groove 3 formed therein.

Alternatively, a thermoplastic polymeric material is arranged on the needlelike object metal mold and is heated to a fusing point or higher until molten. Thereafter, the groove metal mold is positioned in relation to the first needlelike-object base and is subjected to press molding. In this manner, the first needlelike-object base 11 with the groove 3 formed therein can be obtained.

The second needlelike-object base material 12 is then prepared. A description will now be made of a case that the second needlelike-object base 12 is used as a covering member without a groove. A second needlelike-object base 12 comprising a needlelike object part 1b and a base-plate part 2b can be obtained by the same method for preparing the first needlelike-object base as described above by using a metal mold having no groove in place of the groove metal mold. The needlelike object part 1b is not provided with a groove, unlike the needlelike object part 1a of the first needlelike-object base 11.

Subsequently, the first needlelike-object base 11 with the groove 3 formed and the second needlelike-object base 12 with no groove formed are positioned in relation to each other, with the needlelike object part 1a and the needlelike object part 1b facing each other, as shown in FIG. 3(b). In the figure, the reference sign 24 denotes a joining plane. By such joining, the needlelike object 13 comprising the joined needlelike object part 1 and the joined base plate part 2 is obtained with a hollow structure part 21 formed inside, as shown in FIG. 3(c). In addition, the hollow structure part 21 comprises an opening 22 in an intermediate part of the joined needlelike object part 1 and another opening 23 in the back face of the joined base plate part 2, as shown in FIG. 3(b).

By modifying the form of the foregoing groove 3 of the first needlelike-object base 11, the hollow structure 21 can be designed in various forms. For example, the position of the opening of the joined needlelike object part 1 may be changed, a plurality of openings may be provided, the hollow part is closed on one side, or the hollow part may be formed in a tapered shape.

Although a case of no groove formed in the second needlelike-object base 12 has been described, a groove may be formed in the second needlelike-object base 12. A more complicated hollow structure part can be formed by providing grooves in both the first needlelike-object base 11 and the second needlelike-object base 12 to be joined together. Therefore, presence or absence of a groove formed in the second needlelike-object base 12 is desirably selected depending on use purposes.

The method of joining the first and second needlelike-object bases is not particularly limited and a known joining method may be appropriately used in consideration of the materials, shapes, or dimensions of the needlelike-object bases. Available joining methods are a laser welding method, a heat welding method, a vibration welding method, an ultrasonic welding method, and a method of bonding with an adhesive. In this joining method, joining faces may be subjected to a process prior to joining in order to improve the joint strength.

In a method for manufacturing a hollow needlelike object, surface wettability of the hollow structure part 21 is desirably controlled in certain cases. However, the practice of changing a surface quality of a micro narrow hole is generally difficult in some cases. In the methods for manufacturing a hollow needlelike object according to the embodiments, changing a surface quality of the groove 3 can be practiced in a stage prior to formation of the hollow structure part 21. Therefore, a sufficient effect of surface quality change can be expected even inside the hollow structure part. When a surface quality is changed, not only is at least the surface of the groove 3 subjected to the alteration but also a surface quality change is desirably performed on an area to form an inner surface of the hollow structure part 21 after being joined, among surfaces of the second needlelike-object base 12. The method for changing a surface quality is not particularly limited and a known method can be appropriately used in accordance with materials of the needlelike-object bases and/or desired surface characteristics. As a surface quality change treatment, a plasma treatment, an etching process, or a film formation treatment may be used, for example.

Through the processes described above, the hollow needlelike object 13 can be obtained as shown in FIG. 3(c). In the hollow needlelike object 13, the joined needlelike object part 1 is a right quadrangular pyramid and has the hollow structure (not shown) which makes the opening 22 in a side face of the joined needlelike object part 1 communicate with the opening (not shown) in the back face of the joined base plate part 2.

In the hollow needlelike object comprising an opening in a side face of the needlelike object part 1 shown in FIG. 3(c), the distal end of the needlelike object can be more sharpened in comparison with a hollow needlelike object comprising an opening at the distal end of the needlelike object part 1. Therefore, a needlelike object with excellent ability to puncture skin can be obtained.

Second Embodiment

In a method for manufacturing a hollow needlelike object, according to the second embodiment, a face of a first needlelike-object base comprising a groove is covered with a second needlelike-object base, and a needlelike object comprising a hollow structure inside can be thereby manufactured. This manufacturing process will now be described with reference to FIGS. 4(a) and 4(b). The second embodiment is configured by partially modifying shapes of a needlelike-object base and a groove according to the first embodiment, as described above with reference to FIGS. 3(a), 3(b), and 3(c).

As shown in FIG. 4(a), a groove 3 of a first needlelike-object base 11 is formed linearly from the apex of a needlelike object part 1a having a shape of a frustum to the back face of a base plate part 2a. Although a needlelike object part 1b of an opposing second needlelike-object base 12 is also a pyramidal frustum, the needlelike object part 1b is shorter than the needlelike object part 1a of the first needlelike-object base 11. As both the needlelike object parts are joined together, a needlelike object 13 comprising a joined needlelike object part 1 of a form shown in FIG. 4(b) and a joined base plate part 2 of a form shown in FIG. 4(b) is obtained. In the figure, the reference sign 24 denotes a composition plane.

In the second embodiment, the hollow structure part 21 has an opening 22 in an intermediate part of the joined needlelike object part 1 and another opening 23 in the back face of the joined base plate part 2.

Figure 4:
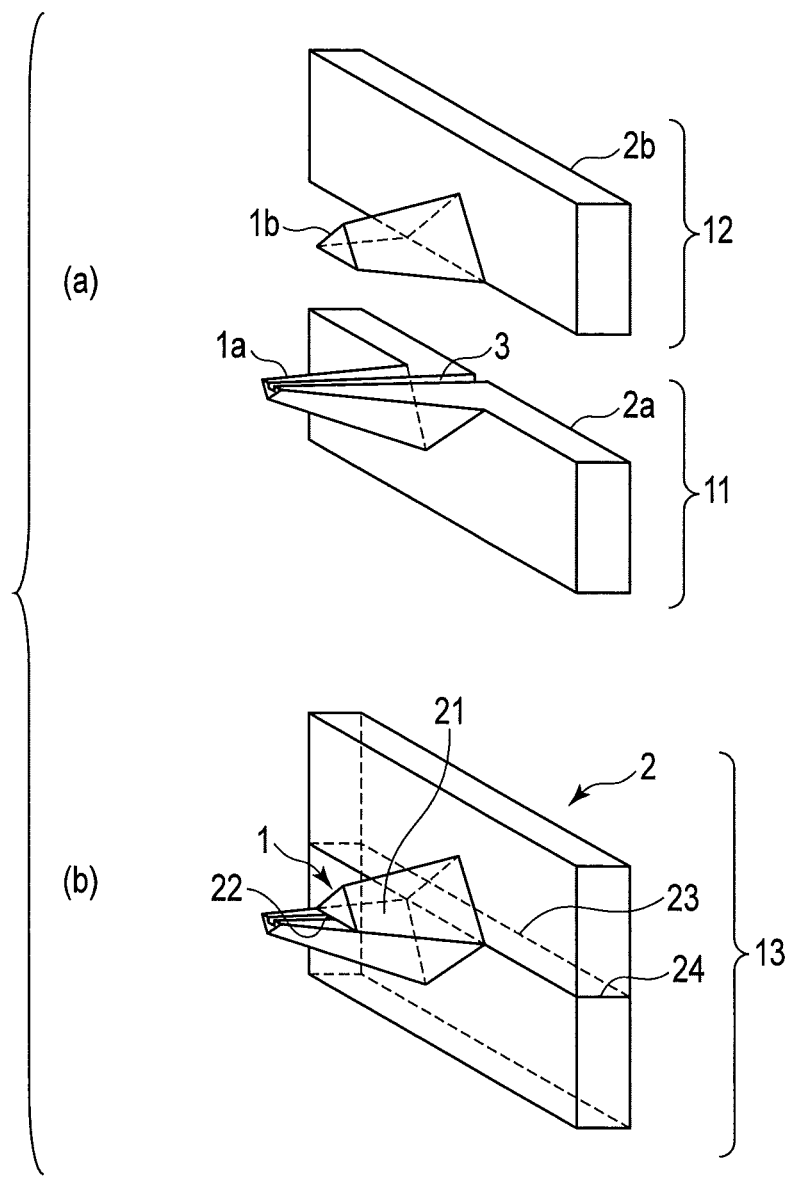
FIG. 4 shows perspective views of a manufacturing process of a hollow needlelike object according to the second embodiment of the present invention.

In the second embodiment, the needlelike object part 1a of the first needlelike-object base 11 and the needlelike object part 1b of the second needlelike-object base 12 have different lengths, respectively, and the joined needlelike object part 1 has a gap in the needlelike object 13 after being joined. An opening 22 is formed at the part of the gap. The needlelike object in the second embodiment is not limited to the structure in which the length of the needlelike object part of the first needlelike-object base having a groove as shown in FIG. 4 is longer than that of the second needlelike-object base. For example, the configuration may be arranged such that the length of the needlelike object part of the first needlelike-object base having a groove is shorter than that of the second needlelike-object base.

In the needlelike object according to the second embodiment, the top does not include a composition plane, and therefore, the distal end of the needlelike object can be formed with high precision only by molding. Therefore, there is an advantage of an excellent ability to puncture skin. Further by providing the first needlelike-object base or the second needlelike-object base at the distal end of the opening 22 formed at the gap part, a space is formed near the opening by the gap when the needlelike object is made to puncture skin. As a result, a needlelike object with excellent liquid injection characteristics for injecting a liquid into skin can be obtained.

Third Embodiment

FIG. 5 is a perspective view showing a method for manufacturing a hollow needlelike object according to the third embodiment. When joining the first and second needlelike-object bases 11 and 12 together, an engagement structure is applied to a base plate part in order to align joining positions. That is, a concave engagement part 31 is provided in an upper part of the base plate part 2a of the first needlelike-object base 11, and a convex engagement part 32 is provided in a base plate part 2b of the second needlelike-object base 12 opposed to the concave engagement part 31. When the first needlelike-object base 11 and second needlelike-object base 12 are joined together, the concave engagement part 31 and the convex engagement part 32 are engaged with each other, and joining positions can be thereby designed precisely. The shape and dimensions of the engagement structure are not particularly limited and may be designed appropriately.

Fourth Embodiment

FIGS. 6(*a*), 6(*b*), and 6(*c*) are perspective views showing manufacturing processes of a hollow needlelike object according to the fourth embodiment. In FIG. 6, a covering member which covers a groove 3 formed in a first needlelike-object base 11 is a sheet 14.

Firstly, the first needlelike-object base 11 comprising the groove 3 and the sheet 14 are prepared as shown in FIG. 6(*a*). The whole surface of a face in which the groove 3 of the first needlelike-object base 11 is formed is covered with the sheet 14 and joined together as shown in FIG. 6(*b*). Subsequently, surplus parts of the sheet 14 which do not cover the first needlelike-object base 11 are removed, and a hollow needlelike object 13 which has a hollow structure as shown in FIG. 6(*c*) is thus formed.

Removal of surplus parts of the sheet 14 can be appropriately performed by use of a known method in consideration of shapes, dimensions, and materials of a needlelike object part 1a and a base plate part 2a. The removal is performed, for example, by a laser method or by an etching method or a sand blast method using the etching selectivity of materials.

The hollow needlelike object according to the fourth embodiment need not be subjected to precise positioning at the time of joining the first and second needlelike-object bases since a sheet member is used as the second needlelike-object base. Therefore, a manufacturing process can be facilitated.

Fifth Embodiment

Figure 7:
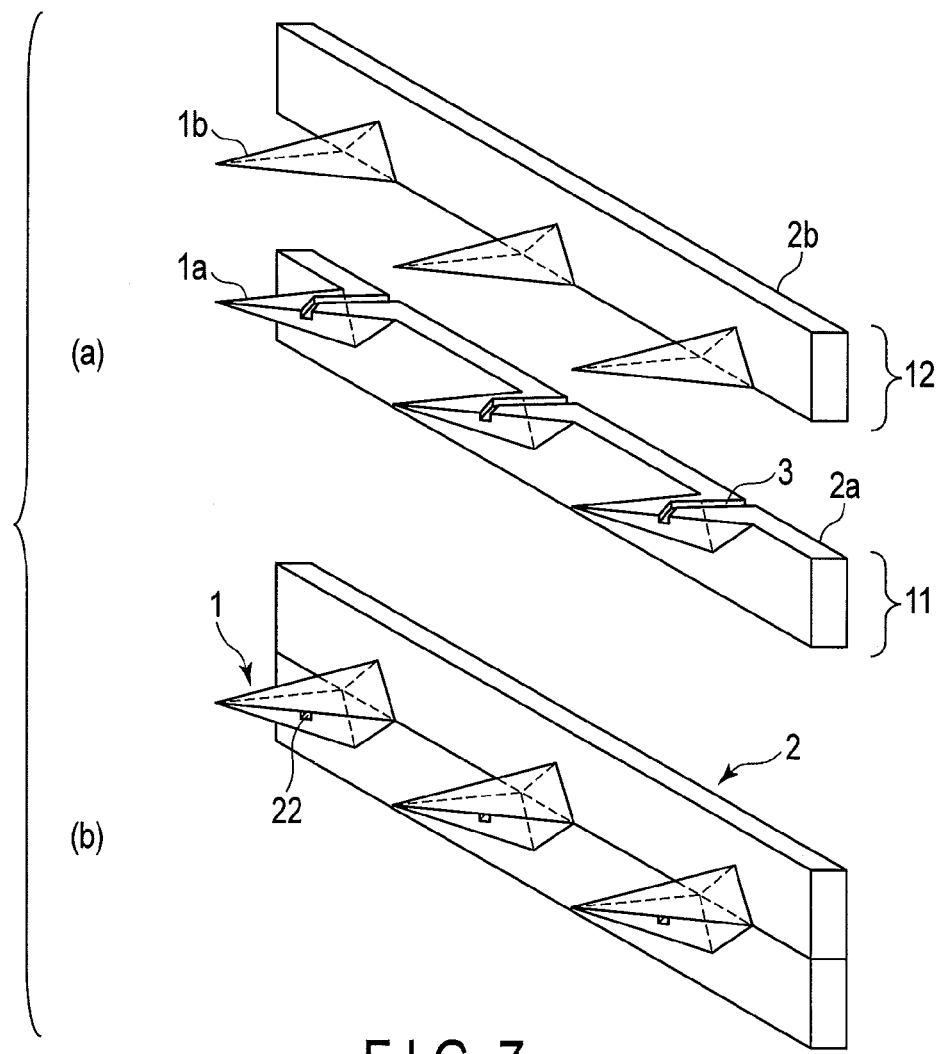
FIG. 7 shows perspective views of a manufacturing process of a hollow needlelike object according to the fifth embodiment of the present invention.

FIGS. 7(*a*) and 7(*b*) are perspective views showing a method for manufacturing a hollow needlelike object, according to the fifth embodiment. Although the foregoing first to fourth embodiments have been described with reference to an example comprising one needlelike object, many needlelike objects arrayed in a row can be manufactured simultaneously, as shown in FIG. 7.

When using a transfer molding method for a polymeric material with use of a metal mold, a metal mold in which a plurality of needlelike objects are arrayed in a row is prepared. A first needlelike-object base 11 and a second needlelike-object base 12 are manufactured as molded products as shown in FIG. 7(*a*). The first needlelike-object base 11 is configured by needlelike object parts 1a and a base plate part 2a, and has a shape such that a plurality of structures each having a groove 3 formed from a needlelike object part 1a to the base plate part 2a are arrayed successively in a row. The second needlelike-object base 12 is configured by needlelike object parts 1b and a base-plate part 2b, and has a shape such that a plurality of structures each forming a needlelike object parts 1b without a groove are arrayed successively in a row. Subsequently, the first and second needlelike-object bases 11 and 12 are joined together, and needlelike objects can be thereby manufactured in which a plurality of hollow needlelike objects are arrayed in a row.

Sixth Embodiment

Figure 8:
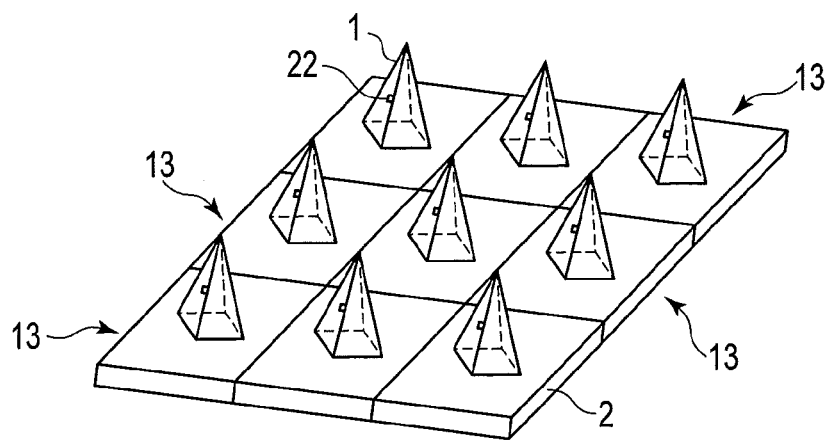
FIG. 8 shows a perspective view of an example of a hollow needlelike object array structure according to the sixth embodiment of the present invention.

FIG. 8 is a perspective view showing a hollow needlelike object according to the sixth embodiment. Needlelike objects 13 each comprising a joined needlelike object part 1 on a sheet of joined base plate part 2 are arrayed in rows and columns. End faces of the joined base plate parts 2 are joined to each other. In this manner, needlelike objects as shown in FIG. 8 can be obtained in which a plurality of joined needlelike object parts 1 are arranged in a matrix array. Alternatively, a plurality of needlelike objects in each of which a plurality of joined needlelike object parts are arrayed in a column may be arranged in a row direction. End faces of joined base plate parts may be joined to each other. Needlelike objects having the same configuration as FIG. 8 can also be thereby obtained. In these cases, a hollow needlelike object can be obtained which comprises a network of flow channels inside the base plate parts if hollow flow channels extending in parallel on surfaces of joined base plate parts 2 are provided in advance inside the joined base plate parts 2 and are further joined together to connect to each other.

Further, through the flow channels, two or more different types of liquids can be fed for each opening.

According to the method described above, a needlelike object can be obtained which has, as a penetration structure, a hollow structure part in which one of openings of a hollow part is formed in a needlelike object, and the other opening is formed in a base plate part (for example, on the back face of the base plate part). In a needlelike object as described above, feeding of a liquid through the needlelike object can be achieved in practice in a facilitated manner by connecting at least one of a liquid feed means and a suction means to openings of the base plate part. The liquid feed means and the suction means each can be a pump or a syringe. In particular, miniaturization of a hollow needlelike object system which has a liquid feed/suction function can be achieved by using a micro pump as a liquid feed/auction means and by joining such means to the base plate part of a hollow needlelike object.

Seventh Embodiment

In a method for manufacturing a hollow needlelike object according to the seventh embodiment, instead of a face of a pyramid including the top thereof, a face of a pyramid not including the distal end is used for a face joining a first needlelike-object base and a second needlelike-object base. In other words, a needlelike object part 1a has a shape such that a right quadrangular pyramid with a truncated top is divided by a face including neither diagonals of a bottom face nor the center axis of the pyramid (or the virtual apex of the pyramid).

A process of covering a face including a groove of a first needlelike-object base with a second needlelike-object base to manufacture a hollow needlelike object according to the seventh embodiment will now be described with reference to FIGS. 9(a), 9(b), and 9(c).

Firstly, as shown in FIG. 9(a), a first needlelike-object base 11 which is configured by a needlelike object part 1a and a base plate part 2a and comprises a groove 3 formed from the needlelike object part 1a to the base plate parts 2a is prepared. The shape of the needlelike object part 1a can be designed appropriately. Here, the needlelike object part 1a has a shape such that a right quadrangular pyramid with a truncated distal end is divided by a face including neither diagonals of a bottom face nor the center axis of the pyramid (or the apex of the pyramid).

Subsequently, the needlelike object part 1a with a groove 3 formed therein and a needlelike object part 1b with no groove formed are positioned in relation to each other and joined together, with the needlelike object part 1a and needlelike object part 1b opposed to each other, as shown in FIG. 9(b). In the figure, the reference sign 24 denotes a composition plane. By joining, a needlelike object 13 comprising a joined needlelike object part 1 and a joined base plate part 2 is obtained with a hollow structure part 21 formed inside, as shown in FIG. 9(c).

Figure 10:
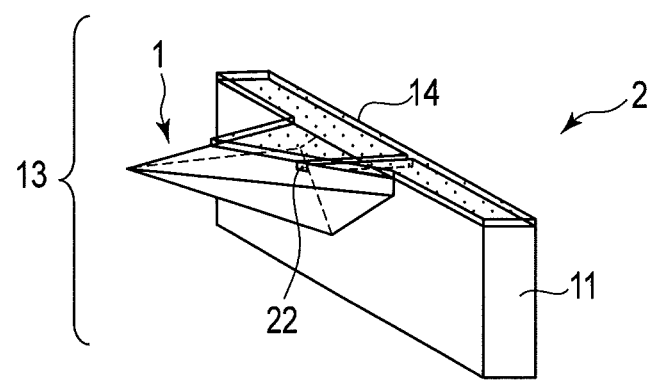
FIG. 10 is a perspective view showing an example of a hollow needlelike object array structure according to the seventh embodiment of the present invention.

FIG. 10 shows a needlelike object having a hollow structure inside and manufactured by covering a face of the first needlelike-object base 11 including the groove 3 with a second needlelike-object base as a sheet 14, as shown in FIG. 9(a).

Since the distal end of the stylus according to the seventh embodiment does not include a joined face, the distal end of the needlelike object according to the seventh embodiment can be formed with high precision only by molding, and has an advantage of excellent ability to puncture skin.

The method for manufacturing a needlelike object according to the present invention is not limited to the embodiments described above and includes a method by which any of respective processes is substituted with any other known process which can be analogized.

As has been described above, according to the embodiments, there is provided a method for manufacturing a hollow needlelike object which comprises a hollow part inside, wherein a first needlelike-object base comprising a groove which divides the hollow needlelike object and forms at least a part of the hollow part, and a covering member are prepared, a face of the first needlelike-object base including the groove is covered with the covering member, and the hollow needlelike object can be thereby manufactured in a facilitated and mass-production manner.

Hereinafter, Examples of the invention will be described with reference to the drawings described previously.

Example 1

Firstly through precision machining, a metal mold was prepared as a concave-convex reversal of a triangular pyramid shape which was obtained by dividing a right quadrangular pyramid having a height of 1000 micrometers and a bottom face having edges each of which was 280 μm long by a face including a diagonal of the bottom face and the apex of the pyramid. Also, through precision machining, a metal mold for forming a groove was prepared which had a protrusion structure with a width of 60 μm and a height of 60 μm. The protrusion structure of the metal mold for forming a groove was designed to position openings in a back face of a base plate part and in an intermediate part (which was approximately 500 μm high) of the needlelike object, and to bend inside the needlelike object.

Subsequently, a first needlelike-object base 11 having a groove 3 in which a needlelike object 1a was held on a base plate part 2a was molded by an injection molding method with use of polypropylene as a molding material and the metal mold for molding a groove. Further, a second needlelike-object base 12 was molded in a form that a needlelike object 1b was held on a base plate part 2b by an injection molding method with use of polypropylene as a molding material and the metal mold subjected to concave-convex reversal of the triangular pyramid shape as described above (shown in FIG. 3(a)). The needlelike-object base 12 had the same shape as the needlelike-object base 11 except that there was no groove.

Subsequently, the first needlelike-object base 11 and the second needlelike-object base 12 were positioned to be opposed to each other while observing the bases with an optical microscope, and were joined together as shown in FIG. 3(b). In this manner, a needlelike object 13 as shown in FIG. 3(c) was obtained which comprised a joined needlelike object part 1 and a joined base plate part 2 with a hollow structure part 21 formed inside.

The joined needlelike object part 1 of the obtained needlelike object 13 has a right quadrangular pyramid shape with a height of 1000 μm and a bottom face having edges each of which was 280 μm long. Further, the joined needlelike object part 1 had a square opening 22 which was approximately 60 μm long in length and width, at a position of the needlelike object height of 500 μm, and another square opening (not shown) which was appropriately 60 μm in length and width, in the back face of the joined base plate part 2. The form as described was checked through observation with a scanning electron microscope. Further, the inside of a hollow structure was observed with a scanning electron microscope to find that areas near the openings form a hollow structure. However, conditions inside could not be observed.

Next, a total of nine needlelike objects 13 were prepared in the same method as above and were joined to each other to obtain a needlelike object array as shown in FIG. 8 in which the needlelike objects 13 were arrayed in a matrix of three rows and three columns with joined needlelike object parts 1 formed on joined base plate parts 2. The back face of a base plate of the needlelike object array was brought into contact with a distal end of a syringe made of plastics, and was joined together by an adhesive so as not to close openings formed in the back face of the needlelike object array.

Pure water was filled inside the syringe, and a pressure was applied to a plunger while observing the joined needlelike object parts 1 with a stereoscopic microscope. Then, pure water was found to be ejected from an intermediate part of each of all nine joined needlelike object parts 1. At this time, no leakage was found from portions joined to the joined base plate parts 2 and the syringe.

From the results described above, the hollow structure parts inside the manufactured needlelike object array were found to be functioning as flow channels.

Example 2

Firstly, through precision machining, as in the Example 1, a metal mold was prepared as a concave-convex reversal of a triangular pyramid shape which was obtained by dividing a right quadrangular pyramid having a height of 1500 μm and a bottom face having edges each of which was 420 μm long, by a face including a diagonal of the bottom face and the apex of the pyramid. Also, through precision machining, a metal mold for forming a groove was prepared which had a protrusion structure with a width of 60 μm and a height of 60 μm. The protrusion structure of the metal mold for forming a groove was designed to position openings in the back face of a base plate part and in an intermediate part (which was approximately 500 μm high) of the needlelike object, and to bend inside the needlelike object.

Subsequently, a first needlelike-object base 11 having a groove 3 in which a needlelike object 1a was held on a base plate part 2a was molded by an injection molding method with use of polypropylene as a molding material and the metal mold for molding a groove. Further, a sheet which was 50 μm thick and made of polypropylene was prepared. (See FIG. 6(*a*))

Subsequently, the first needlelike-object base plate and the polypropylene sheet were joined as shown in FIG. 6(*b*). Finally, surplus parts of the polypropylene sheet which were not joined to the first needlelike-object base plate were removed by a laser. A needlelike object 13 as shown in FIG. 6(*c*) was then obtained which comprised a joined needlelike object part 1 and a joined base plate part 2 with a hollow structure part 21 formed inside.

The joined needlelike object part 1 of the obtained needlelike object 13 had a triangular pyramid shape obtained by dividing, into two, a right quadrangular pyramid shape with a height of appropriately 1000 μm and a bottom face having edges each of which was appropriately 280 μm long. Further, the joined needlelike object part 1 had a square opening 22 which was appropriately 60 μm long in length and width, at a position of the needlelike object height of approximately 500 μm, and another square opening (not shown) which was appropriately 60 μm in length and width in the back face of the joined base plate part 2. The form as described was checked by observation with a scanning electron microscope.

Next, the back face of a base plate of a needlelike object array was brought into contact with a distal end of a syringe made of plastics, and was joined by an adhesive so as not to close openings formed in the back face of the needlelike object array. Pure water was filled in the syringe, and a pressure was applied to a plunger while observing the joined needlelike object part 1 with a stereoscopic microscope. As a result, pure water was found to be ejected from intermediate parts of the joined needlelike object parts 1. At this time, no leakage was found from portions joined to the joined base plate parts 2 and the syringe.

From the results described above, the hollow structure parts inside the manufactured needlelike object array were found to be functioning as flow channels.

Example 3

Firstly, through precision machining, as in the Example 1, a metal mold was prepared as a concave-convex reversal of a triangular pyramid shape which was obtained by dividing a right quadrangular pyramid having a height of 1000 μm and a bottom face having edges each of which was 280 μm long, by a face including a diagonal of the bottom face and the apex of the pyramid. Also, through precision machining, a metal mold for forming a groove was prepared which had a protrusion structure with a width of 60 μm and a height of 60 μm, and had a convex shape in a base plate part. The protrusion structure of the metal mold for forming a groove was designed to position openings in the back face of a base plate part and in an intermediate part (which was approximately 500 μm high) of the needlelike object, and to bend inside the needlelike object.

Further, a second metal mold having a concave shape which was a reversal of the convex shape of the metal mold for a groove was prepared.

Subsequently, a first needlelike-object base 11 having a groove 3 and a concave shape 31 in which a needlelike object 1a was held on a base plate part 2a was molded by an injection molding method with use of polypropylene as a molding material and the metal mold for molding a groove. Further, a second needlelike-object base 12 having a convex shape 32 was molded in which a needlelike object 1a was held on a base plate part 2a by an injection molding method with use of polypropylene as a molding material and the metal mold and the second metal mold (see FIG. 5).

Subsequently, the first needlelike-object base 11 and the second needlelike-object base 12 were positioned to be opposed to each other while observing the bases with an optical microscope, and were joined together. In this manner, a needlelike object 13 was obtained which comprised a joined needlelike object part 1 and a joined base plate part 2 with a hollow structure part 21 formed inside. At this time, the time needed for position alignment could be shortened in comparison with a process of joining the first needlelike-object base 11 and the second needlelike-object base 12 according to the Example 1.

The obtained needlelike object was found to be the same as that in Example 1 by observation with a scanning electron microscope. Further, the back face of a base plate of a needlelike object array was brought into contact with a distal end of a syringe made of plastics, and was joined by an adhesive so as not to close openings formed in the back face of the needlelike object array. Pure water was filled in the syringe, and a pressure was applied to a plunger while observing the joined needlelike object part 1 with a stereoscopic microscope. As a result, pure water was found to be ejected from intermediate parts of the joined needlelike object parts 1. At this time, no leakage was found from portions joined to the joined base plate parts 2 and the syringe.

From the results described above, the hollow structure parts inside the manufactured needlelike object array were found to be functioning as flow channels.

A hollow needlelike object obtained by a manufacturing method according to the present invention is applicable not only to medical care but also to various fields which require a micro needlelike object. The hollow needlelike object is expected to be suitably used in a process of manufacturing, for example, a semiconductor device, an optical element, a wiring circuit, a storage device (a hard disk or a DVD), a distal end part for medical inspections (DNA-analysis use), a display panel, a micro flow channel, a micro reactor, a MEMS device, a probe tip of an inspection device, a field emission element, drug development, or cosmetics.

The invention claimed is:

1. A method for manufacturing a hollow needlelike object comprising a hollow part inside, the method comprising:
preparing a first needlelike-object base that includes a half needlelike object part having a longitudinal axis, a sharp distal end and a wide proximal end positioned along the longitudinal axis and a tapered intermediate side surface between the sharp distal end and the wide proximal end, a base plate part provided on a wide bottom end of the half needlelike object part, and a flat face extending along the longitudinal axis of the half needlelike object part on the half needlelike object part and the base plate part, the flat face comprising a groove forming the hollow part, extending from the base plate part to an intermediate part of the half needlelike object part, bent in a lateral direction, and having an outlet in the tapered intermediate side surface; and
covering the flat face of the needlelike-object base with a covering member.

2. The method for manufacturing a hollow needlelike object according to claim 1, wherein the covering member is a second needlelike-object base which forms the hollow needlelike object in combination with the first needlelike-object base or a sheet member which forms the hollow needlelike object in combination with the first needlelike-object base.

3. The method for manufacturing a hollow needlelike object according to claim 1, wherein the base plate includes a back face that is opposite to the half needlelike object part and the groove in the base plate part is opened in the back face of the base plate part.

4. The method for manufacturing a hollow needlelike object according to claim 1, wherein the first needlelike-object base has a structure in which a plurality of half needlelike object parts are arrayed in a row on the base plate part and a plurality of covering members are arrayed In a row, and a plurality of hollow needlelike objects arrayed in a row on the base plate part are obtained by covering the flat faces of the half needlelike object parts with a plurality of covering members.

5. The method for manufacturing a hollow needlelike object according to claim 1, wherein the needlelike-object base and the covering member are made of a biodegradable material.

6. The method for manufacturing a hollow needlelike object according to claim 1, further comprising performing a surface treatment at least on a surface of the groove of the first needlelike-object base.

7. The method for manufacturing a hollow needlelike object according to claim 1, wherein the groove is branched in the base plate and the branched grooves extend in a lateral direction in the base plate.

8. The method for manufacturing a hollow needlelike object according to claim 2, wherein the second needlelike-object base includes a half needlelike object part having a longitudinal axis, a sharp distal end and a wide proximal ends positioned along the longitudinal axis and a tapered intermediate side surface between the sharp distal end and the wide proximal end,
a base plate part provided on the wide bottom end of the half needlelike object part, and
a flat face extending along the longitudinal axis of the half needlelike object part on the half needlelike object part and the base plate part, and
the base plate parts of the first needlelike-object base and second needlelike-object base are provided with an engagement structure for aligning joining positions of the base plate parts of the first needlelike-object base and second needlelike-object base.

9. The method for manufacturing a hollow needlelike object according to claim 8, wherein the engagement structure includes a concave engagement part provided on one of the base plate parts of the first needlelike-object base and second needlelike-object base and a convex engagement part provided on the other of the base plates of the first needlelike-object base and second needlelike-object base.

10. A hollow needlelike object manufactured by the method for manufacturing a hollow needlelike object according to claim 1.

11. A hollow needlelike object comprising a hollow part inside, comprising:
a first needlelike-object base including:
a half needlelike object part having a longitudinal axis, a sharp distal end and a wide proximal end positioned along the longitudinal axis and a tapered intermediate side surface between the sharp distal end and the wide proximal end,
a base plate part provided on a wide bottom end of the half needlelike object part, and
a flat face extending along the longitudinal axis of the half needlelike object part on the half needlelike object part and the base plate part, the flat face comprising a groove forming the hollow part, extending from the base plate part to an intermediate part of the half needlelike object part, bent in a lateral direction, and having an outlet in the tapered intermediate side surface; and
a covering member joined to the first needlelike-object base and covering the flat face of the first needlelike-object base.

12. The hollow needlelike object according to claim 11, wherein the covering member is a second needlelike-object base which forms the hollow needlelike object in combination with the first needlelike-object base or a sheet member which forms the hollow needlelike object in combination with the first needlelike-object base.

13. The hollow needlelike object according to claim 11, wherein the base plate includes a back face that is opposite to the half needlelike object part and the groove in the base plate part is opened in the back face of the base plate part.

14. The hollow needlelike object according to claim 11, wherein the first needlelike-object base has a structure in which a plurality of half needlelike objects are arrayed in a row on the base plate part and a plurality of covering members are arrayed in a row, and a plurality of hollow needlelike objects arrayed in a row on the base plate part are obtained by covering the flat faces of the half needlelike object parts with a plurality of covering members.

15. The hollow needlelike object according to claim 11, wherein the groove is branched in the base plate and the branched grooves extend in a lateral direction in the base plate.

16. The hollow needlelike object according to claim 12, wherein the second needlelike-object base includes a half needlelike object part having a longitudinal axis, a sharp distal end and a wide proximal ends positioned along the longitudinal axis and a tapered intermediate side surface between the sharp distal end and the wide proximal end,
- a base plate part provided on the wide bottom end of the half needlelike object part, and
- a flat face extending along the longitudinal axis of the half needlelike object part on the half needlelike object part and the base plate part, and
- the base plate parts of the first needlelike-object base and second needlelike-object base are provided with an engagement structure for aligning joining positions of the base plate parts of the first needlelike-object base and second needlelike-object base.

17. The hollow needlelike object according to claim 16, wherein the engagement structure includes a concave engagement part provided on one of the base plate parts of the first needlelike-object base and second needlelike-object base and a convex engagement part provided on the other of the base plates of the first needlelike-object base and second needlelike-object base.

* * * * *

UNITED STATES PATENT AND TRADEMARK OFFICE
CERTIFICATE OF CORRECTION

PATENT NO. : 9,533,131 B2
APPLICATION NO. : 14/260766
DATED : January 3, 2017
INVENTOR(S) : Hiroshi Sugimura It is certified that error appears in the above-identified patent and that said Letters Patent is hereby corrected as shown below:

In the Claims

Column 15, Line 44, Claim 4:
Delete "In" and insert -- in --, therefor.

Signed and Sealed this
Fourteenth Day of March, 2017

Michelle K. Lee
*Director of the United States Patent and Trademark Office*